(12) United States Patent
Risch et al.

(10) Patent No.: US 7,087,794 B2
(45) Date of Patent: *Aug. 8, 2006

(54) OXYGENATE CONVERSION IN THE PRESENCE OF HIGHLY UNSATURATED COMPOUNDS

(75) Inventors: Michael A. Risch, Seabrook, TX (US); John Di-Yi Ou, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 721 days.

This patent is subject to a terminal disclaimer.

(21) Appl. No.: 10/295,419

(22) Filed: Nov. 15, 2002

(65) Prior Publication Data
US 2004/0097760 A1    May 20, 2004

(51) Int. Cl.
- *C07C 45/00* (2006.01)
- *C07C 41/00* (2006.01)
- *C07C 2/00* (2006.01)

(52) U.S. Cl. ............ 568/405; 568/485; 568/671; 585/500

(58) Field of Classification Search ............ None
See application file for complete search history.

(56) References Cited

U.S. PATENT DOCUMENTS

| | | | |
|---|---|---|---|
| 3,725,493 A | 4/1973 | Stine | 260/680 |
| 4,367,353 A | 1/1983 | Inglis | 585/258 |
| 4,587,373 A | 5/1986 | Hsia | 585/639 |
| 4,625,050 A | 11/1986 | Current | 560/232 |
| 4,912,281 A | 3/1990 | Wu | 585/640 |
| 5,491,273 A | 2/1996 | Santiesteban | 585/639 |
| 5,837,217 A | 11/1998 | Nielsen et al. | 423/648.1 |
| 6,084,140 A | 7/2000 | Kitamura et al. | 585/260 |
| 6,169,218 B1 | 1/2001 | Hearn et al. | 585/260 |
| 6,413,449 B1 | 7/2002 | Wieland et al. | 252/373 |
| 6,717,025 B1 * | 4/2004 | Risch et al. | 585/804 |

FOREIGN PATENT DOCUMENTS

| | | |
|---|---|---|
| DE | 2 720 749 | 11/1978 |
| DE | 3 210 756 | 9/1983 |
| EP | 229 994 | 5/1989 |
| EP | 0 665 205 | 8/1995 |
| EP | 0 504 980 | 9/2002 |
| GB | 873873 | 2/1961 |
| WO | WO 02/26669 | 4/2002 |

* cited by examiner

*Primary Examiner*—Sikarl A. Witherspoon

(57) ABSTRACT

The present invention provides a process for treating a stream, say, an olefins stream, e.g., propylene, containing at least one ether, e.g., dimethyl ether, and/or at least one of an alkyne and an alkadiene, e.g., methyl acetylene and propadiene, typically present as impurities. The process comprises: contacting the stream with a metal-containing catalyst, e.g., palladium supported on alumina, under conditions sufficient to convert the ether and the at least one of an alkyne and an alkadiene to provide a product stream having a reduced impurities content.

110 Claims, No Drawings

OXYGENATE CONVERSION IN THE PRESENCE OF HIGHLY UNSATURATED COMPOUNDS

FIELD

The present invention relates to a method for treating streams in the presence of oxygenates, such as $C_2$ to $C_6$ ether, and at least one highly unsaturated compound, e.g., alkyne and/or alkadienes.

BACKGROUND

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins is oxygenate, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins generates by-products whose presence is undesirable for subsequent applications of the collected olefins. Although the separation of many oxygenates, e.g., ketones and aldehydes, from hydrocarbons such as olefins can be capably handled by existing commercial processes, the separation of other oxygenates, e.g., dimethyl ether (DME) can be problematic.

DME is an oxygenate impurity formed during the conversion of methanol into light olefins which can act as a poison to downstream olefin polymerization catalysts, especially metallocene catalysts. Removal of DME from oxygenates to olefins product streams is thus highly desirable. Unfortunately, such removal can be difficult given, inter alia, DME's physical characteristics similar to certain lower olefins, e.g., its similar volatility to propylene. Separation of DME from propylene by distillation, e.g., using a $C_3$ splitter, requires a super fractionation column requiring significant capital investment. Alternatively, DME's difference in solubility from lower olefins can be exploited by using a water wash to remove DME from an olefinic product stream. Unfortunately, given DME's non-polar characteristics, an extensive volume of water would be required in a water wash tower so employed. Given these difficulties it would be desirable to provide a process for removing DME from olefin-containing streams such as those obtained by conversion of oxygenates to olefins, which does not require super-fractionation or water washing.

Methods for recovering and recycling dimethylether (DME) from a methanol-to-chemical conversion reaction using a DME absorber tower are disclosed in U.S. Pat. No. 4,587,373 to Hsia. Stud. Surf. Sci. Catal. (1985), 20 (Catl. Acids Bases), 391–8, discusses low temperature conversion of dimethyl ether over Pt/H-ZSM-5 in the presence of hydrogen by a bifunctionally catalyzed reaction. Stud. Surf. Sci. Catal. (1993), 77 discusses hydrogenation of oxygenates such as dimethyl ether over a $Ni/Al_2O_3$ catalyst to form methane. U.S. Pat. No. 5,491,273 to Chang et al. discloses conversion of lower aliphatic alcohols and corresponding ethers to linear olefins over large crystal zeolites, e.g., ZSM-35 containing a hydrogenation component of Group VIA and Group VIIIA metals. DE3210756 discloses a process for converting methanol and/or dimethyl ether feed to olefins by reacting the feed over a pentasil type zeolite catalyst, separating $C_2$–$C_4$ olefins, methane and water from the reaction product and catalytically hydrogenating the remaining components over Co—Mo supported on alumina, optionally preceded by hydrogenation over a Group 8 noble metal for polyunsaturated, non-aromatic compounds. U.S. Pat. No. 4,912,281 to Wu discloses converting methanol or methyl ether to light olefins in the presence of hydrogen and ZSM-45 which is highly selective to $C_2$–$C_4$ olefins, especially ethylene. DE2720749 discloses converting lower aliphatic ethers to hydrocarbons in the presence of amorphous, non-acid-activated Al silicate. U.S. Pat. No. 4,625,050 to Current discloses the use of carbonylation to convert dimethyl ether to methyl acetate and ethanol (as well as minor amounts of methyl formate and propanol) over hydrogen and CO in the presence of heterogeneous NiMo catalyst on an alumina support. EP-229994 discloses the removal of DME as an impurity (1–500 wppm) of olefinic hydrocarbon feedstock by passing the feedstock through an adsorbent mass of crystalline zeolite molecular sieve having the crystal structure of faujasite at 0°–60° C. and 0.15–500 psia to selectively absorb DME. All of the above references are incorporated herein by reference in their entirety.

In addition to DME, light olefin products, especially those generated by steam cracking or derived from oxygenated feedstocks, can contain unsaturated by-products such as acetylene, methyl acetylene (MA) and propadiene (PD). Making olefins from oxygenated feedstocks produces a unique effluent stream that must ultimately be separated and purified to produce the high purity olefin products currently desired. These unsaturated by-products poison polyolefin catalysts, and therefore must be almost completely removed from olefin product streams. For ethylene, current manufacturing specifications can require acetylene levels to be under 0.5 mole ppm. For propylene, current manufacturing specifications can require methyl acetylene and propadiene levels to be under 2.9 mole ppm.

Catalysts for selectively hydrogenating highly unsaturated compounds are known in the art. For example, U.S. Pat. No. 6,084,140 to Kitamura et al. discloses a palladium and alumina catalyst for hydrogenating highly unsaturated hydrocarbons in olefin streams from steam cracking processes. The catalyst can hydrogenate acetylene, methyl acetylene, and propadiene, with only limited hydrogenation of the olefin products. U.S. Pat. No. 4,367,353 to Inglis discusses a hydrogenation process using a supported palladium catalyst. The process involves first fractionating the hydrocarbon streams before hydrogenating whereby hydrogen is removed. Hydrogen is added during a subsequent hydrogenation step, allowing for greater control of the extent of hydrogenation. Because the concentration of unsaturated by-products acetylene, methyl acetylene, and propadiene can increase to three times their initial amounts during the purification of the hydrocarbons by fractionation, the concentration of acetylene, methyl acetylene and propadiene must be three times lower in front-end hydrogenation than in tail end hydrogenation. Achieving this greater purity results in greater loss of olefin products during the hydrogenation process. U.S. Pat. No. 5,837,217 to Nielsen et al. discloses preparation of hydrogen rich gas from a feed stock of dimethyl ether and steam, wherein the dimethyl ether is reacted with steam in the presence of i) an ether hydration catalyst such as acidic zeolites, e.g. HZSM-5, and ii) a methanol decomposition catalyst, e.g., Cu—Zn-alumina. U.S. Pat. No. 6,413,449 to Wieland et al. discloses a catalyst comprising palladium/zinc alloy and zinc oxide as catalytically active components useful for the steam reforming of alcohols, e.g., methanol to produce hydrogen-rich gas. All of the above references are incorporated herein by reference in their entirety.

Given the difficulties presented in separately removing by-products DME and the unsaturated compounds methyl acetylene, propadiene and acetylene from olefinic product streams, particularly those product streams from steam cracking and oxygenate to olefins processes, it would be advantageous to remove at least one or more of these by-products with techniques that do not require dedicated equipment for superfractionation, water washing, etc. Moreover, it would be advantageous to at least partially remove these by-products using equipment commonly found in existing olefin plant recovery trains, e.g., hydrogenation reactors. Accordingly, it would be particularly advantageous to remove DME along with the hydrocarbon impurities acetylene, methyl acetylene, and propadiene from the product stream using the same equipment.

SUMMARY

In one aspect, the present invention relates to a process for chemically converting $C_2$ to $C_6$ ether to at least one other oxygenate compound. The process comprises: contacting a feedstream comprising $C_2$ to $C_6$ ether and at least one of at least one alkyne and at least one alkadiene, with a metal-containing catalyst under conditions sufficient to convert the $C_2$ to $C_6$ ether to the at least one other oxygenate compound, the at least one other oxygenate compound comprising: at least one of $C_3$ to $C_{12}$ ether, $C_3$ to $C_{13}$ ketone and $C_3$ to $C_7$ aldehyde, thereby providing a converted stream.

In one embodiment of this aspect of the invention, the $C_2$ to $C_6$ ether is selected from dimethyl ether, methyl ethyl ether, methyl propyl ether, methyl butyl ether, diethyl ether, ethyl propyl ether, ethyl butyl ether, di-n-propyl ether, and di-isopropyl ether, say, dimethyl ether, the alkyne is selected from acetylene, methyl acetylene, ethyl acetylene and dimethyl acetylene, say, methyl acetylene, and the alkadiene is selected from propadiene, 1,2 butadiene and 1,3-butadiene, say, propadiene. Typically, the converted stream comprises at least one of acetone, methyl n-propyl ether and methyl-isopropyl ether.

In another embodiment of this aspect of the invention, the at least one other oxygenate compound is heavier than the $C_2$ to $C_6$ ether, Typically, the process further comprises removing the at least one other oxygenate compound from the converted stream. Such removing can be carried out by distillation.

In still another embodiment, the converting is carried out in the vapor phase under conditions which comprise temperatures ranging from about 0° C. to about 800° C., total pressures ranging from about 101 kPaa to about 7 MPaa (from about 0 psig to about 1000 psig), GHSVs ranging from about 10 to about 30000, and hydrogen partial pressures ranging from 0 kPaa to about 2170 kPAA (from about 0.0 psig to about 300 psig). In another embodiment, the converting is carried out in the vapor phase under conditions which comprise temperatures ranging from about 20° C. to about 600° C., total pressures ranging from about 101 kPaa to about 4240 kPaa (from about 0 psig to about 600 psig), GHSVs ranging from about 100 to about 20000, and hydrogen partial pressures ranging from about 0 kPaa to about 1480 kPaa (about 0.0 psig to about 200 psig).

In still another embodiment, the converting is carried out in the liquid phase under conditions which comprise temperatures ranging from about 0° C. to about 100° C., total pressures ranging from about 790 kPaa to about 7 MPaa (from about 100 psig to about 1000 psig), LHSVs ranging from about 0.01 to about 1000, and a hydrogen/(alkyne+alkadiene) ratio ranging from about 0 to about 1000 on a molar basis. Typically, the converting is carried out in the liquid phase under conditions which comprise a temperature ranging from about 20° C. to about 80° C., total pressures ranging from about 1140 kPaa to about 4240 kPaa (from about 150 psig to about 600 psig), LHSVs ranging from about 0.1 to about 100, and a hydrogen/(alkyne+alkadiene) ratio ranging from about 0 to about 100 on a molar basis.

In one embodiment of this aspect of the invention, feedstream contains at least about 0.5:1 molar ratio of the sum of said alkyne and alkadiene to said $C_2$ to $C_6$ ether. Typically, the feedstream comprises from about 1 to about 5000 mppm (mole ppm) dimethyl ether, say, from about 1 to about 1000 mppm dimethyl ether, e.g., from about 1 mppm to about 500 mppm dimethyl ether; from about 50 to about 100 mol % $C_2$ to $C_4$ olefin, say, from about 75 to about 100 mol % $C_2$ to $C_4$ olefin, and from about 1 mppm to about 20 mol % of the at least one of at least one alkyne and at least one alkadiene say, from about 1 mppm to about 10 mol % of said at least one of at least one alkyne and at least one alkadiene. The converting of the feedstream can be carried out in a preferred embodiment without substantially converting said $C_2$ to $C_4$ olefin, i.e., no greater than about 5% conversion, e.g., no greater than about 1% conversion.

In yet another embodiment of this aspect, the feedstream comprises from about 75 to 100 mol % propylene, from about 1 mppm to about 4 mol % methyl acetylene, and from about 1 mppm to about 5 mol % propadiene.

In still another embodiment of this aspect of the invention, at least about 20 mol % of said $C_2$ to $C_6$ ether and at least about 20 mol % of said at least one of an alkyne and an alkadiene is converted. Typically, at least about 50 mol % of said dimethyl ether and at least about 50 mol % of the total of said at least one of methyl acetylene and propadiene are converted.

In another embodiment, the converting provides at least partial hydrogenation of said at least one of at least one alkyne and at least one alkadiene, of at least about 20 mol %. The at least partial hydrogenation can provide at least one of ethylene, propylene, 1-butene, 2-butene and isobutene.

In still another embodiment, the metal-containing catalyst comprises i) at least one member selected from the group consisting of group 8 (VIIIA) metals, group 8 (VIIIA) metal compounds, group 9 (VIIIA) metals, group 9 (VIIIA) metal compounds, group 10 (VIIIA) metals, group 10 (VIIIA) metal compounds, group 11 (IB) metals, and group 11 (IB) metal compounds, of the Periodic Table, and ii) at least one of at least one porous inorganic oxide, at least one microporous crystalline molecular sieve, and a carbon. Such catalysts can be prepared in accordance with the below-described techniques used for making oxygenate to olefins catalysts, e.g., by impregnating a catalyst substrate with a metal or metal ion-containing solution and thereafter drying and/or calcining the resulting composite.

In yet another embodiment, the catalyst comprises palladium, e.g., the catalyst comprises palladium and silver.

In another embodiment of this aspect of the present invention, the catalyst comprises at least one of i) at least one porous inorganic oxide selected from the group consisting of oxides of elements selected from Group 2, Group 3, Group 4, Group 5, Zn, Group 13, Si, Ge, Sn, Pb, P, As, Sb and Bi, ii) at least one microporous crystalline molecular sieve selected from the group consisting of silicates, aluminosilicates, substituted aluminosilicates, aluminophosphates, and substituted aluminophosphates, and iii) a carbon. The catalyst can further comprise iv) at least one of a sulfur-containing moiety and oxygen-containing moiety.

In yet another embodiment, the catalyst comprises palladium on an alumina substrate and contains from about 0.01 to about 4.0 wt % Pd, say, from about 0.015 to about 1.0 wt % Pd.

In still another embodiment of the process of the invention, the feedstream is prepared by: exposing an oxygenate feed with an olefin generation catalyst under conditions sufficient to provide a first product stream which contains water, $C_{5+}$ organic compounds, $C_2$ to $C_4$ olefins, oxygenates comprising dimethyl ether, and unsaturated $C_2$ to $C_4$ by-products comprising at least one of at least one alkyne and at least one alkadiene; and at least partially removing the water, $C_{5+}$ organic compounds, and oxygenates comprising dimethyl ether from the first product stream to provide a second product stream enriched in $C_2$ to $C_4$ olefins and unsaturated $C_2$ to $C_4$ by-products comprising at least one of at least one alkyne and at least one alkadiene, and containing reduced amounts of oxygenate impurities comprising dimethyl ether, relative to said first product stream.

In another aspect, the present invention relates to a process for treating an olefin stream in the presence of at least one ether and at least one of at least one alkyne and at least one alkadiene, the process comprising: contacting the olefin stream with a metal-containing catalyst under conditions sufficient to convert the ether and the at least one of at least one alkyne and at least one alkadiene to provide a product stream. Typically, the ether is $C_2$ to $C_6$ ether, e.g., an ether selected from dimethyl ether, methyl ethyl ether, methyl propyl ether, methyl butyl ether, diethyl ether, ethyl propyl ether, ethyl butyl ether, di-n-propyl ether, and di-isopropyl ether. Said alkyne can be selected from acetylene, methyl acetylene, ethyl acetylene and dimethyl acetylene, and said alkadiene can be selected from propadiene, 1,2 butadiene and 1,3-butadiene.

In one embodiment of this aspect of the invention, the product stream comprises at least one of $C_3$ to $C_{12}$ ether, $C_3$ to $C_{13}$ ketone and $C_3$ to $C_7$ aldehyde.

In another embodiment, the $C_2$ to $C_6$ ether comprises dimethyl ether, said alkyne comprises methyl acetylene, said alkadiene comprises propadiene and the product stream comprises at least one of acetone, methyl n-propyl ether and methylisopropyl ether.

In still another embodiment, the product stream comprises at least one oxygenate compound heavier than the $C_2$ to $C_6$ ether; and which further comprises removing, say, by distillation, the at least one oxygenate compound heavier than the $C_2$ to $C_6$ ether from said converted stream.

In another embodiment of this aspect of the invention, the olefin stream contains at least about 0.5:1 molar ratio of the sum of said alkyne and alkadiene to said $C_2$ to $C_6$ ether. Typically, the olefin stream comprises from about 1 to about 5000 mppm dimethyl ether, say, from about 1 to about 1000 mppm dimethyl ether, e.g., from about 1 ppm to about 500 ppm dimethyl ether, from about 50 to about 100 wt % $C_2$ to $C_4$ olefin, say, from about 75 to about 100 wt % $C_2$ to $C_4$ olefin, e.g., from about 75 to 100 wt % propylene, and from about 1 ppm to about 20 mol % of said at least one of at least one alkyne and at least one alkadiene, say, from about 1 ppm to about 10 mol % of said at least one of at least one alkyne and at least one alkadiene.

In another aspect, the present invention relates to a process for removing ether from a stream, the process comprising: a) contacting the stream with a metal-containing catalyst in the presence of a total molar ratio of at least about 0.5:1, of at least one of at least one alkyne and at least one alkadiene to the ether and optionally, in the presence of hydrogen, and the contacting being under conditions sufficient to convert the said ether to at least one other oxygenate, thereby reducing the content of said ether in said stream; and b) exposing the stream with a metal-containing catalyst in the presence of hydrogen under conditions sufficient to at least partially convert the at least one of at least one alkyne and at least one alkadiene in said stream to a mono-olefin, thereby reducing the content of said alkyne and alkadiene in said stream. In one embodiment of this aspect of the invention, the said at least one other oxygenate comprises at least one of $C_3$ to $C_{12}$ ether, $C_3$ to $C_{13}$ ketone and $C_3$ to $C_7$ aldehyde.

In another embodiment, the said at least one other oxygenate comprises at least one oxygenate compound heavier than said $C_2$ to $C_6$ ether; and which further comprises at least partially removing said mono-olefin. Typically, said removing is carried out by distillation.

In yet another embodiment, the contacting conditions are vapor phase and comprise temperatures ranging from about 0° C. to about 800° C., total pressures ranging from about 101 kPaa to about 7 MPaa (from about 0.1 psig to about 1000 psig), GHSVs ranging from about 10 to about 30000, and optionally, hydrogen partial pressures ranging from about 0 kPaa to about 2170 kPaa (from about 0 psig to about 300 psig; and said exposing conditions comprise temperatures ranging from about 0° C. to about 800° C., total pressures ranging from about 101 kPaa to about 7 mPaa (from about 0.1 psig to about 1000 psig), GHSVs ranging from about 10 to about 30000 and hydrogen partial pressures ranging from about 0 kPaa to about 2170 kPaa (from about 0 psig to about 300 psig).

In still yet another embodiment, the contacting conditions are vapor phase and comprise temperatures ranging from about 20° C. to about 600° C., total pressures ranging from about 101 kPaa to about 4240 kPaa (from about 0 psig to about 600 psig), GHSVs ranging from about 100 to about 20000, and optionally, hydrogen partial pressures ranging from about 0 kPaa to about 1480 kPaa (about 0 psig to about 200 psig); and the exposing conditions comprise temperatures ranging from about 20° C. to about 600° C., total pressures ranging from about 101 kPaa to about 4240 kPaa (from about 0 psig to about 600 psig), GHSVs ranging from about 100 to about 20000, and hydrogen partial pressures ranging from about 0 kPaa to about 1480 kPaa (about 0 psig to about 200 psig).

In yet another embodiment, the contacting conditions are liquid phase and comprise temperatures ranging from about 0° C. to about 100° C., total pressures ranging from about 790 kPaa to about 7 MPaa (from about 100 psig to about 1000 psig), LHSVs ranging from about 0.01 to about 1000, and optionally, a hydrogen/(alkyne+alkadiene) ratio ranging from about 0 to about 1000 on a molar basis; and the exposing conditions comprise temperatures ranging from about 0° C. to about 100° C., total pressures ranging from about 790 kPaa to about 7 MPaa (from about 100 psig to about 1000 psig), LHSVs ranging from about 0.01 to about 1000, and a hydrogen/(alkyne+alkadiene) ratio ranging from about 0 to about 1000 on a molar basis.

In still another embodiment, the contacting conditions are liquid phase and comprise temperatures ranging from about 20° C. to about 80° C., total pressures ranging from about 1140 kPaa to about 4240 kPaa (from about 150 psig to about 600 psig), and LHSVs ranging from about 0.1 to about 100, and optionally, a hydrogen/(alkyne+alkadiene) ratio ranging from about 0 to about 100 on a molar basis; and said exposing conditions temperatures ranging from about 20° C. to about 80° C., total pressures ranging from about 1140 kPaa to about 4240 kPaa (from about 150 psig to about 600 psig), and LHSVs ranging from about 0.1 to about 100, and a hydrogen/(alkyne+alkadiene) ratio ranging from about 0 to about 100 on a molar basis.

In another embodiment of this aspect of the invention, the stream comprises from about 1 to about 5000 mppm dimethyl ether, from about 50 to about 100 wt % $C_2$ to $C_4$ olefin, and from about 1 mppm to about 20 mol % of the at least one of at least one alkyne and at least one alkadiene. Typically, the contacting and the exposing are carried out without substantially converting the $C_2$ to $C_4$ olefin.

In yet another embodiment, the stream comprises from about 1 to about 1000 mppm dimethyl ether, from about 75 to about 100 wt % $C_2$ to $C_4$ olefin, and from about 1 mppm to about 10 mol % of the at least one of at least one alkyne and at least one alkadiene.

In still another embodiment, the stream comprises from about 1 mppm to about 500 mppm dimethyl ether, from about 75 to 100 wt % propylene, from about 1 mppm to about 4 mol % methyl acetylene, and from about 1 mppm to about 5 mol % propadiene.

In still yet another embodiment, the exposing provides at least partial hydrogenation of said at least one of at least one alkyne and at least one alkadiene, of at least about 20 mol %.

In another embodiment, the at least partial hydrogenation provides at least one of ethylene, propylene, 1-butene, 2-butene and isobutene.

In still another embodiment of this aspect of the invention, the process comprises carrying out a) and b) under substantially the same conditions.

In yet another embodiment, the process comprises carrying out a) and b) under substantially different conditions.

In another embodiment, the process comprises carrying out a) and b) in series wherein a) is carried out prior to b).

In yet another embodiment, the process comprises carrying out a) and b) in series wherein b) is carried out prior to a).

In another embodiment, the process comprises combining a) and b) in-situ and carrying out a) and b) simultaneously.

In still yet another embodiment of this aspect of the invention, the olefin stream contains at least one ether and the process further comprises: adding at least one of at least one alkyne and at least one alkadiene to the olefin stream to provide a total molar ratio of at least one of at least one alkyne and at least one alkadiene to said ether, of at least about 0.5:1; said contacting providing a product stream of reduced said ether content.

In another embodiment of this aspect of the invention, the olefin stream contains at least one of at least one alkyne and at least one alkadiene and the process further comprises: adding at least one ether to the olefin stream to provide a total molar ratio of ether to said at least one of at least one alkyne and at least one alkadiene, of no greater than about 2:1; said contacting providing a product stream of reduced said at least one of at least one alkyne and at least one alkadiene content.

In another aspect the present invention relates to a process for treating an olefin stream containing impurities comprising at least one ether and at least one of at least one alkyne and at least one alkadiene, the process comprising: contacting the olefin stream with a metal-containing catalyst under conditions sufficient to convert the at least one ether and the at least one of at least one alkyne and at least one alkadiene to provide a product stream having a reduced impurities content.

In yet another aspect, the present invention relates to a process for removing dimethyl ether from an olefin stream containing propylene, the process comprising: contacting the olefin stream in the presence of a metal-containing catalyst and at least one of methyl acetylene and propadiene under conditions sufficient to convert at least some of the dimethyl ether to another oxygenate.

In one embodiment, the another oxygenate is heavier than the dimethyl ether; and the process further comprises at least partially removing said another oxygenate, e.g., by distillation. Typically, the contacting is carried out without substantially converting the propylene.

In another embodiment, the olefin stream comprises from about 1 to about 5000 mppm dimethyl ether, from about 50 to about 100 wt % propylene, and from about 1 mppm to about 20 mol % of the at least one of methyl acetylene and propadiene.

In yet another embodiment, the olefin stream comprises from about 1 to about 1000 mppm dimethyl ether, from about 75 to about 100 wt % propylene, and from about 1 mppm to about 10 mol % of said at least one of methyl acetylene and propadiene.

In still another embodiment, the olefin stream comprises from about 1 mppm to about 500 mppm dimethyl ether, from about 75 to about 100 wt % propylene, from about 1 mppm to about 4 mol % methyl acetylene, and from about 1 mppm to about 5 mol % propadiene.

In still yet another embodiment, at least about 20 mol % of said dimethyl ether and at least about 20 mol % of said at least one of methyl acetylene and propadiene are converted.

DETAILED DESCRIPTION

Molecular Sieves and Catalysts Thereof

Molecular sieves suited to use in the present invention for converting oxygenates to olefins have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of*

*Zeolite Framework Types,* 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPSO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon cocatalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthamides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis: $mR:(M_xAl_yP_z)O_2$ wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthamide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butylamine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

Polymeric bases, especially polymeric bases that are soluble or non-ionic, useful in the invention, are those having a pH sufficient to control the pH desired for synthesizing a given molecular sieve, especially a SAPO molecular sieve. In a preferred embodiment, the polymeric base is soluble or the polymeric base is non-ionic, preferably the polymeric base is a non-ionic and soluble polymeric base, and most preferably the polymeric base is a polymeric imine. In one embodiment, the polymeric base of the invention has a pH in an aqueous solution, preferably water, from greater than 7 to about 14, more preferably from about 8 to about 14, most preferably from about 9 to 14.

In another embodiment, the non-volatile polymeric base is represented by the formula: $(R-NH)_x$, where (R—NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000. In one embodiment, R is a linear, branched, or cyclic polymer, monomeric, chain, preferably a linear polymer chain having from 1 to 20 carbon atoms.

In another embodiment, the polymeric base is a water miscible polymeric base, preferably in an aqueous solution. In yet another embodiment, the polymeric base is a polyethylenimine that is represented by the following general formula: $(-NHCH_2CH_2-)_m[-N(CH_2CH_2NH_2)CH_2CH_2-]_n)$, wherein m is from 10 to 20,000, and n is from 0 to 2,000, preferably from 1 to 2000.

In another embodiment, the polymeric base of the invention has a average molecular weight from about 500 to about 1,000,000, preferably from about 2,000 to about 800,000, more preferably from about 10,000 to about 750,000, and most preferably from about 50,000 to about 750,000.

In another embodiment, the mole ratio of the monomeric unit of the polymeric base of the invention, containing one basic group, to the templating agent(s) is less than 20, preferably less than 12, more preferably less than 10, even more preferably less than 8, still even more preferably less than 5, and most preferably less than 4.

Non-limiting examples of polymer bases include: epichlorohydrin modified polyethylenimine, ethoxylated polyethylenimine, polypropylenimine diamine dendrimers (DAB-Am-n), poly(allylamine) $[CH_2CH(CH_2NH_2)]_n$, poly (1,2-dihydro-2,2,4-trimethylquinoline), and poly(dimethylamine-co-epichlorohydrin-co-ethylenediamine).

In another embodiment the invention is directed to a method for synthesizing a molecular sieve utilizing a templating agent, preferably an organic templating agent such as an organic amine, an ammonium salt and/or an ammonium hydroxide, in combination with a polymeric base such as polyethylenimine.

In a typical synthesis of the molecular sieve, the phosphorous-, aluminum-, and/or silicon-containing components are mixed, preferably while stirring and/or agitation and/or seeding with a crystalline material, optionally with an alkali metal, in a solvent such as water, and one or more templating agents and a polymeric base, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference. The polymeric base is combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent and polymeric base, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Another method of crystallization is directed to not stirring a reaction mixture, for example a reaction mixture containing at a minimum, a silicon-, an aluminum-, and/or a phosphorous-composition, with a templating agent and a polymeric base, for a period of time during crystallization. See PCT WO 01/47810 published Jul. 5, 2001, which is herein fully incorporated by reference.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No.

5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, a templating agent, and a polymeric base should be in the range of from 2 to 10, preferably in the range of from 4 to 9, and most preferably in the range of from 5 to 8. The pH can be controlled by the addition of basic or acidic compounds as necessary to maintain the pH during the synthesis in the preferred range of from 4 to 9. In another embodiment, the templating agent and/or polymeric base is added to the reaction mixture of the silicon source and phosphorous source such that the pH of the reaction mixture does not exceed 10.

In one embodiment, the molecular sieves of the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and FischerTropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

Method for Making Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material (s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference.

The process for converting a feedstock, especially a feedstock containing one or more oxygenates, in the presence of a molecular sieve catalyst composition according to the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

Oxygenate to Olefins Process

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s)

include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly, or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is selected from group 13 (IIIA), groups 8, 9 and 10 (VIII) elements) from the Periodic Table of Elements), and a molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kpaa) to about 500 psia (3448 kpaa), preferably from about 20 psia (138 kPaa) to about 250 psia (1724 kpaa), more preferably from about 25 psia (172 kPaa) to about 150 psia (1034 kPaa), and most preferably from about 30 psia (207 kpaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are disclosed in U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 weight percent coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, for reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No.

6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

The present invention solves the current needs in the art by providing a method for converting a feed including an oxygenate to a product including a light olefin. The method of the present invention is conducted in a reactor apparatus As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

A preferred embodiment of a reactor system for the present invention is a circulating fluid bed reactor with continuous regeneration, similar to a modern fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a coke content on regenerated catalyst of no greater than 10 carbon atoms per acid site of the molecular sieve in the catalyst, or the formulated catalyst itself. At least a portion of the regenerated catalyst should be returned to the reactor.

Treatment of Product Effluent Containing Oxygenate and Highly Unsaturated By-Products The present invention is particularly suited to the treating or converting of various streams that contain oxygenates. Such treating or converting is further carried out in the presence of at least one highly unsaturated compound, e.g., at least one of alkynes, dienes, and trienes, e.g., at least one of an alkyne and an alkadiene. The highly unsaturated compound may be present in the stream as an impurity or alternatively, may be added to the stream prior to the treating or converting step. Conversely, the present invention is also suited to the treating or converting of various streams which contain at least one highly unsaturated compound, e.g., at least one of alkynes, dienes, and trienes, e.g., at least one of an alkyne and an alkadiene. Such treating or converting is further carried out in the presence of an oxygenate, e.g., ether. The oxygenate may be present in the stream as an impurity or alternatively, may be added to the stream prior to the treating or converting step.

The present invention, while useful for treating any oxygenate-containing stream in the presence of highly unsaturated compounds, is especially suited to treating olefin streams derived from oxygenates to olefin effluents which contain unacceptable amounts of ethers and highly unsaturated by-products of the oxygenates to olefin process. Typical product streams from oxygenates to olefin conversion contain water, $C_{5+}$ organic compounds, $C_2$ to $C_4$ olefins, oxygenates comprising dimethyl ether, and unsaturated $C_2$ to $C_4$ by-products comprising at least one of an alkyne and an alkadiene. Such streams can be treated in accordance with the present invention by at least partially removing the water, $C_{5+}$ organic compounds, and oxygenates comprising dimethyl ether to provide a treated stream enriched in $C_2$ to $C_4$ olefins and unsaturated $C_2$ to $C_4$ by-products comprising at least one of an alkyne and an alkadiene, and containing reduced amounts of oxygenate impurities comprising dimethyl ether.

Oxygenate Impurity Conversion Catalyst

Typically, the present invention utilizes a catalyst comprising a member selected from the group consisting of metals and metal based compounds, including those described above as being useful for oxygenate to olefins conversion. In one embodiment, the catalyst comprises at least one member selected from the group consisting of, group 8 (VIIIA) metals, group 8 (VIIIA) metal compounds, group 9 (VIIIA) metals, group 9 (VIIIA) metal compounds, group 10 (VIIIA) metals, group 10 (VIIIA) metal compounds, group 11 (IB) metals, and group 11 (IB) metal compounds. (Arabic numerals relate to the newer IUPAC 18 column format whilst Roman numerals relate to 1970 IUPAC rules.)

Catalysts suited for use in embodiments of the present invention wherein oxygenate impurities are converted include those which function in the presence of hydrogen as well as those that function in the absence of hydrogen. Exemplary of both are hydrogenation catalysts, such as a supported metal catalyst, e.g., supported noble metal catalyst.

Hydrogenation catalysts are especially suited for use in those embodiments of the present invention. An example of such a hydrogenation catalyst comprises a hydrogenation catalyst comprising i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one member selected from the group consisting of a porous inorganic oxide (as described above) and microporous crystalline molecular sieve (as described above). Exposure to such catalyst simultaneously effects 1) conversion of said dimethyl ether, and 2) at least partial hydrogenation of said member selected from the group consisting of alkyne and alkadiene. Preferably, the catalyst comprises at least one member selected from the group consisting of group 10 (VIII) metal, e.g., palladium, which in one embodiment is supported by an inorganic oxide. Alternatively, the catalyst can comprise at least one of i) at least one porous inorganic oxide selected from the group of oxides of elements of groups 2–5, Zn, groups 13, 14 (excluding carbon), and 15 (excluding nitrogen), and ii) at least one microporous crystalline molecular sieve selected from the group consisting of silicates, aluminosilicates, substituted aluminosilicates, aluminophosphates, and substituted aluminophosphates. In yet another embodiment, the catalyst can further comprise iii) a member selected from the group consisting of a sulfur-containing moiety and oxygen-containing moiety. Examples of such catalysts are commercially available under the trade name C31-1-01, from Sud-Chemie of Louisville, Ky., and contain a minimum of 0.03 wt. % palladium supported on alumina.

The foregoing catalysts employed in converting oxygenate impurities can be deactivated during use and can be at least partially regenerated in accordance with the techniques described above for oxygenate conversion catalysts, as well as any other suitable regeneration technique know to those skilled in the art.

Oxygenate Impurity Conversion Reactors

Suitable oxygenate impurity conversion reactors for converting olefinic streams containing oxygenate impurities in the presence of a catalyst or supported metal catalyst composition of the invention, include a fixed bed reactor or a fluidized bed reactor, desirably a fixed bed reactor. The reactor can be operated isothermally or adiabatically. For those embodiments of the present invention where the highly unsaturated alkynes and alkadienes are hydrogenated to olefins during oxygenate impurity conversion, adiabatic operation of the reactor is preferred.

Oxygenate Impurity Conversion Conditions

In one aspect, the present invention utilizes oxygenate impurity conversion conditions which are sufficient to convert an oxygenate impurity in the treated stream to a heavier oxygenate compound.

In the present invention, oxygenate impurity converting can be carried out in the liquid phase and comprises a temperature ranging from about 0° C. to about 100° C., total pressures ranging from about 790 kPaa to about 7 MPaa (from about 100 psig to about 1000 psig), LHSV ranging from about 0.01 to about 1000, and a hydrogen/(alkyne+alkadiene) ratio ranging from about 0 to about 1000 on a molar basis, preferably comprising a temperature ranging from about 20° C. to about 80° C., total pressures ranging from about 1140 kPaa to about 4240 kPaa (from about 150 psig to about 600 psig), LHSV ranging from about 0.1 to about 100, and a hydrogen/(alkyne+alkadiene) ratio ranging from about 0 to about 100 on a molar basis.

Alternatively, the converting of oxygenate impurity can be carried out in the vapor phase and comprises a temperature ranging from about 0° C. to about 800° C., total pressures ranging from about 101 kPaa to about 7 MPaa (from about 0 psig to about 1000 psig), GHSV (gas hourly space velocity) ranging from about 10 to about 30,000, and a hydrogen partial pressure ranging from about 0 kPaa to about 2170 kpaa (from about 0 psig to about 300 psig), preferably comprising a temperature ranging from about 20° to about 600° C., total pressures ranging from about 101 kpaa to about 4240 kPaa (from about 0 psig to about 600 psig), GHSV ranging from about 100 to about 20,000, and hydrogen partial pressure ranging from about 0 kpaa to about 1480 kPaa (ranging from about 0 psig to about 200 psig).

Typically, conversion of oxygenate impurities in a treated stream according to the present invention, can be at least about 10%, at least about 20%, at least about 50%, at least about 80%, or even at least about 90%, especially for dimethyl ether conversion to higher boiling compounds.

These conditions are typically sufficient to provide conversion of oxygenate impurity without substantially converting olefins present in the stream being treated. By "substantially converting" is meant that no greater than about 5 wt %, no greater than about 1 wt %, or even no greater than about 0.1 wt % of $C_2$ to $C_6$ olefin is converted, singly or in the aggregate. Moreover, these conditions can include the presence or absence of hydrogen depending on the stream being treated and the desired product resulting from conversion of oxygenate impurity. In those embodiments carried out in the vapor phase in the presence of hydrogen, partial pressures of hydrogen range from about 101.4 kPaa to about 2170 kPaa (about 0.02 to about 300 psig), preferably from about 102.8 kPaa to about 1825 kPaa (about 0.2 to about 250 psig), and most preferably from about 115 kPaa to about 1480 kPaa (about 2 to about 200 psig). In those embodiments carried out in the liquid phase in the presence of hydrogen, hydrogen/(alkyne+alkadiene) ratio range from about 001 to about 1000 on a molar basis, preferably from 0.05–500, and most preferably from about 0.1–100. In cases wherein the treated stream contains a member selected from the group consisting of alkyne and alkadiene, at least partial hydrogenation of a member selected from the group consisting of alkyne and alkadiene can be by at least about 10%, at least about 25%, or even at least about 50%. Such products of the at least partial hydrogenation are selected from at least one of ethylene, propylene, and butenes.

The following example illustrates, but does not limit, the present invention.

EXAMPLE

A feed was treated in accordance with the present invention. The feed comprised dimethyl ether, methyl acetylene, and propadiene, which were simultaneously converted over a commercial gas-phase methyl acetylene/propadiene (MAPD) hydrogenation catalyst obtained from SCI of Louisville, Ky., USA. The catalyst was reduced under hydrogen at 232° C. (450° F.) and 360 GHSV and then cooled to reaction temperature under helium flow. Hydrocarbon was fed to the reactor at a rate of 3.2 WHSV (960 GHSV). The feed consisted of 84.13 mol % propylene, 9.56 mol % propane, 2.63 mol % methyl acetylene, 3.68 mol % propadiene and 183 ppm dimethyl ether. Hydrogen was co-fed to attain varying $H_2$/MAPD (hydrogen to methyl acetylene and propadiene) molar ratios.

Table 1 shows a typical hydrocarbon product distribution at 209° C. and approximately 310 psig. Under these conditions, MAPD conversion was about 87 mol %. In addition, a DME conversion of about 50 mol % is attained.

Major oxygenate products included acetone and methyl isopropyl ether, which could be easily separated from light olefins in a depropanizer distillation column. Table 2 shows a product distribution from the converted DME.

TABLE 1

Reaction Conditions and Product Distribution from MAPD Conversion

| | |
|---|---|
| WHSV ($h^{-1}$) | 3.2 |
| Temperature (° C.) | 209 |
| Pressure kPaa (psig) | 2240 (309.6) |
| $H_2$/MAPD (mol) | 1.10 |
| FEED (mol % except as noted) | |
| $C_3=$ | 84.13 |
| $C_3$ | 9.56 |
| Methyl Acetylene | 2.63 |
| Propadiene | 3.68 |
| DME (ppm) | 183 |
| PRODUCT | |
| $C_1$ | 0.00 |
| $C_2=$ | 0.05 |
| $C_2$ | 0.01 |
| $C_3$ | 11.26 |
| Methyl Acetylene | 0.26 |
| Propadiene | 0.56 |
| $iC_4$ and $nC_4$ | 0.03 |
| $C_4=$ | 0.03 |
| $C_4==$ | 0.04 |
| $C_5s$ | 0.02 |
| $C_6s$ | 0.26 |
| Benzene | 0.00 |
| $C_6s+$ | 0.08 |
| DME (ppm) | 93 |
| Estimated Oxygenates (ppm) | 90 |

TABLE 2

Distribution of Oxygenated Products

| Oxygenate Product | Selectivity (mol %) |
|---|---|
| Methyl Isopropyl Ether | 56.7 |
| Acetone | 27.7 |
| Isopropanol | 7.1 |
| Methanol | 5.4 |
| Diisopropyl Ether | 3.2 |

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. A process for chemically converting $C_2$ to $C_6$ ether to at least one other oxygenate compound, the process comprising:
contacting a feedstream comprising $C_2$ to $C_6$ ether and at least one of at least one alkyne and at least one alkadiene, with a metal-containing catalyst under conditions sufficient to convert said $C_2$ to $C_6$ ether to said at least one other oxygenate compound, the at least one other oxygenate compound comprising: at least one of $C_3$ to $C_{12}$ ether, $C_3$ to $C_{13}$ ketone and $C_3$ to $C_7$ aldehyde, thereby providing a converted stream.

2. The process of claim 1 wherein said $C_2$ to $C_6$ ether is selected from dimethyl ether, methyl ethyl ether, methyl propyl ether, methyl butyl ether, diethyl ether, ethyl propyl ether, ethyl butyl ether, di-n-propyl ether, and di-isopropyl ether, said alkyne is selected from acetylene, methyl acetylene, ethyl acetylene and dimethyl acetylene, and said alkadiene is selected from propadiene, 1,2 butadiene and 1,3-butadiene.

3. The process of claim 1 wherein said $C_2$ to $C_6$ ether comprises dimethyl ether, said alkyne comprises methyl acetylene, said alkadiene comprises propadiene and said converted stream comprises at least one of acetone, methyl n-propyl ether and methylisopropyl ether.

4. The process of claim 1 wherein said at least one other oxygenate compound is heavier than said $C_2$ to $C_6$ ether; and which further comprises removing said at least one other oxygenate compound from said converted stream.

5. The process of claim 4 wherein said removing is carried out by distillation.

6. The process of claim 1 wherein said converting is carried out in the vapor phase under conditions which comprise temperatures ranging from about 0° C. to about 800° C., total pressures ranging from about 101 kPaa to about 7 MPaa (from about 0 psig to about 1000 psig), GHSVs ranging from about 10 to about 30000, and hydrogen partial pressures ranging from about 0 kPaa to about 2170 kPaa (from about 0 psig to about 300 psig).

7. The process of claim 1 wherein said converting is carried out in the vapor phase under conditions which comprise temperatures ranging from about 20° C. to about 600° C., total pressures ranging from about 101 kPaa to about 4240 kPaa (from about 0 psig to about 600 psig), GHSVs ranging from about 100 to about 20000, and hydrogen partial pressures ranging from about 0 kPaa to about 1480 kPaa (from about 0 psig to about 200 psig).

8. The process of claim 1 wherein said converting is carried out in the liquid phase under conditions which comprise temperatures ranging from about 0° C. to about 100° C., total pressures ranging from about 790 kPaa to about 7 MPaa (from about 100 psig to about 1000 psig), LHSVs ranging from about 0.01 to about 1000, and a hydrogen/(alkyne+alkadiene) ratio ranging from about 0 to about 1000 on a molar basis.

9. The process of claim 1 wherein said converting is carried out in the liquid phase under conditions which comprise temperatures ranging from about 20° C. to about 80° C., total pressures ranging from about 1140 kpaa to about 4240 kPaa (from about 150 psig to about 600 psig), LHSVs ranging from about 0.1 to about 100, and a hydrogen/(alkyne+alkadiene) ratio ranging from about 0 to about 100 on a molar basis.

10. The process of claim 1 wherein said feedstream contains at least about 0.5:1 molar ratio of the sum of said alkyne and alkadiene to said $C_2$ to $C_6$ ether.

11. The process of claim 1 wherein said feedstream comprises from about 1 to about 5000 mppm dimethyl ether, from about 50 to about 100 wt % $C_2$ to $C_4$ olefin, and from about 1 mppm to about 20 mol % of said at least one of at least one alkyne and at least one alkadiene.

12. The process of claim 11 wherein said converting is carried out without substantially converting said $C_2$ to $C_4$ olefin.

13. The process of claim 1 wherein said feedstream comprises from about 1 to about 1000 mppm dimethyl ether, from about 75 to about 100 wt % $C_2$ to $C_4$ olefin, and from about 1 mppm to about 10 mol % of said at least one of an alkyne and an alkadiene.

14. The process of claim 1 wherein said feedstream comprises from about 1 ppm to about 500 mppm dimethyl ether, from about 75 to 100 wt % propylene, from about 1 mppm to about 4 mol % methyl acetylene, and from about 1 mppm to about 5 mol % propadiene.

15. The process of claim 1 wherein at least about 20 mol % of said $C_2$ to $C_6$ ether and at least about 20 mol % of said at least one of at least one alkyne and at least one alkadiene are converted.

16. The process of claim 2 wherein at least about 50 mol % of said dimethyl ether and at least about 50 mol % of the total of said at least one of methyl acetylene and propadiene are converted.

17. The process of claim 1 wherein said converting provides at least partial hydrogenation of said at least one of at least one alkyne and at least one alkadiene, of at least about 20 mol %.

18. The process of claim 17 wherein said at least partial hydrogenation provides at least one of ethylene, propylene, 1-butene, 2-butene and isobutene.

19. The process of claim 1 wherein said metal-containing catalyst comprises i) at least one member selected from the group consisting of group 8 (VIIIA) metal, group 8 (VIIIA) metal compound, group 9 (VIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one of at least one porous inorganic oxide, at least one microporous crystalline molecular sieve and a carbon.

20. The process of claim 19 wherein said catalyst comprises palladium.

21. The process of claim 19 wherein said catalyst comprises palladium and silver.

22. The process of claim 19 wherein said catalyst comprises at least one of i) at least one porous inorganic oxide selected from the group consisting of oxides of elements selected from group 2, group 3, group 4, group 5, Zn, group 13, Si, Ge, Sn, Pb, P, As, Sb and Bi, ii) at least one microporous crystalline molecular sieve selected from the group consisting of silicates, aluminosilicates, substituted aluminosilicates, aluminophosphates, and substituted aluminophosphates, and iii) a carbon.

23. The process of claim 22 wherein said catalyst further comprises iv) at least one of a sulfur-containing moiety and an oxygen-containing moiety.

24. The process of claim 20 wherein said catalyst comprises palladium on an alumina substrate and contains from about 0.01 to about 4.0 wt % palladium.

25. The process of claim 1 wherein said feedstream is prepared by:
 exposing an oxygenate feed with an olefin generation catalyst under conditions sufficient to provide a first product stream which contains water, $C_{5+}$ organic compounds, $C_2$ to $C_4$ olefins, oxygenates comprising dimethyl ether, and unsaturated $C_2$ to $C_4$ by-products comprising at least one of at least one alkyne and at least one alkadiene; and
 at least partially removing said water, $C_{5+}$ organic compounds, and oxygenates comprising dimethyl ether from said first product stream to provide a second product stream enriched in $C_2$ to $C_4$ olefins and unsaturated $C_2$ to $C_4$ by-products comprising at least one of at least one alkyne and at least one alkadiene, and containing reduced amounts of oxygenate impurities comprising dimethyl ether, relative to said first product stream.

26. A process for treating an olefstream in the presence of at least one ether and at least one of at least one alkyne and at least one alkadiene, the process comprising:
 contacting said olefin stream with a metal-containing catalyst under conditions sufficient to convert said at least one ether and said at least one of at least one alkyne and at least one alkadiene to provide a product stream.

27. The process of claim 26 wherein said olefin stream contains said at least one ether and which further comprises:
 adding at least one of at least one alkyne and at least one alkadiene to said olefin stream to provide a total molar ratio of said at least one of at least one alkyne and at least one alkadiene to said at least one ether, of at least about 0.5:1;
 said contacting providing a product stream of reduced said at least one ether content.

28. The process of claim 26 wherein said olefin stream contains at least one of at least one alkyne and at least one alkadiene and which further comprises:
 adding at least one ether to said olefin stream to provide a total molar ratio of said at least one ether to said at least one of at least one alkyne and at least one alkadiene, of no greater than about 2:1;
 said contacting providing a product stream of reduced said at least one of at least one alkyne and at least one alkadiene content.

29. The process of claim 26 wherein said at least one ether is $C_2$ to $C_6$ ether.

30. The process of claim 29 wherein said $C_2$ to $C_6$ ether is selected from dimethyl ether, methyl ethyl ether, methyl propyl ether, methyl butyl ether, diethyl ether, ethyl propyl ether, ethyl butyl ether, di-n-propyl ether, and di-isopropyl ether, said alkyne is selected from acetylene, methyl acetylene, ethyl acetylene and dimethyl acetylene, and said alkadiene is selected from propadiene, 1,2-butadiene and 1,3-butadiene.

31. The process of claim 27 wherein said product stream comprises at least one of $C_3$ to $C_{12}$ ether, $C_3$ to $C_{13}$ ketone and $C_3$ to $C_7$ aldehyde.

32. The process of claim 30 wherein said $C_2$ to $C_6$ ether comprises dimethyl ether, said alkyne comprises methyl acetylene, said alkadiene comprises propadiene and said product stream comprises at least one of acetone, methyl n-propyl ether and methylisopropyl ether.

33. The process of claim 29 wherein said product stream comprises at least one oxygenate compound heavier than said $C_2$ to $C_6$ ether; and which further comprises removing said at least one oxygenate compound heavier than said $C_2$ to $C_6$ ether from said product stream.

34. The process of claim 33 wherein said removing is carried out by distillation.

35. The process of claim 33 wherein said converting is carried out in the vapor phase under conditions which comprise temperatures ranging from about 0° C. to about 800° C., total pressures ranging from about 101 kPaa to about 7 MPaa (from about 0 psig to about 1000 psig), GHSVs ranging from about 10 to about 30000, and hydrogen partial pressures ranging from about 0 kpaa to about 2170 kPaa (from about 0 psig to about 300 psig).

36. The process of claim 33 wherein said conditions are vapor phase and comprise temperatures ranging from about 20° C. to about 600° C., total pressures ranging from about 101 kPaa to about 4240 kPaa (from about 0 psig to about 600 psig), GHSVs ranging from about 100 to about 20000, and hydrogen partial pressures ranging from about 0 kPaa to about 1480 kPaa (from about 0 psig to about 200 psig).

37. The process of claim 33 wherein said converting is carried out in the liquid phase under conditions which comprise temperatures ranging from about 0° C. to about 100° C., total pressures ranging from about 790 kPaa to about 7 MPaa (from about 100 psig to about 1000 psig), LHSVs ranging from about 0.01 to about 1000, and a hydrogen/(alkyne+alkadiene) ratio ranging from about 0 to about 1000 on a molar basis.

38. The process of claim 33 wherein said conditions are liquid phase and comprise temperatures ranging from about 20° C. to about 80° C., total pressures ranging from about 1140 kPaa to about 4240 kPaa (from about 150 psig to about 600 psig), LHSVs ranging from about 0.1 to about 100, and a hydrogen/(alkyne+alkadiene) ratio ranging from about 0 to about 100 on a molar basis.

39. The process of claim 33 wherein said olefin stream contains at least about 0.5:1 molar ratio of the sum of said alkyne and alkadiene to said $C_2$ to $C_6$ ether.

40. The process of claim 33 wherein said olefin stream comprises from about 1 to about 5000 mppm dimethyl ether, from about 50 to about 100 wt % $C_2$ to $C_4$ olefin, and from about 1 mppm to about 20 mol % of said at least one of at least one alkyne and at least one alkadiene.

41. The process of claim 40 wherein said converting is carried out without substantially converting said $C_2$ to $C_4$ olefin.

42. The process of claim 33 wherein said olefin stream comprises from about 1 to about 1000 mppm dimethyl ether, from about 75 to about 100 wt % $C_2$ to $C_4$ olefin, and from about 1 mppm to about 10 mol % of said at least one of at least one alkyne and at least one alkadiene.

43. The process of claim 33 wherein said olefin stream comprises from about 1 to about 500 mppm dimethyl ether, from about 75 to 100 wt % propylene, from about 1 mppm to about 4 mol % methyl acetylene, and from about 1 mppm to about 5 mol % propadiene.

44. The process of claim 33 wherein at least about 20 mol % of said $C_2$ to $C_6$ ether and at least about 20 mol % of said at least one of at least one alkyne and at least one alkadiene are converted.

45. The process of claim 30 wherein at least about 50 mol % of said dimethyl ether and at least about 50 mol % of the total of said at least one of methyl acetylene and propadiene are converted.

46. The process of claim 33 wherein said contacting provides at least partial hydrogenation of said at least one of at least one alkyne and at least one alkadiene, of at least about 20 mol %.

47. The process of claim 46 wherein said at least partial hydrogenation provides at least one of ethylene, propylene, 1-butene, 2-butene and isobutene.

48. The process of claim 26 wherein said metal-containing catalyst comprises i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one of at least one porous inorganic oxide, at least one microporous crystalline molecular sieve, and a carbon.

49. The process of claim 48 wherein said catalyst comprises palladium.

50. The process of claim 48 wherein said catalyst comprises palladium and silver.

51. The process of claim 48 wherein said catalyst comprises at least one of i) at least one porous inorganic oxide selected from oxides of elements selected from group 2, group 3, group 4, group 5, Zn, group 13, Si, Ge, Sn, Pb, P, As, Sb and Bi, ii) at least one microporous crystalline molecular sieve selected from silicates, aluminosilicates, substituted aluminosilicates, aluminophosphates, and substituted aluminophosphates, and iii) a carbon.

52. The process of claim 51 wherein said catalyst further comprises iv) at least one of a sulfur-containing moiety and oxygen-containing moiety.

53. The process of claim 49 wherein said catalyst comprises palladium on an alumina substrate and contains from about 0.01 to about 4.0 wt % palladium.

54. A process for removing at least one of at least one ether, at least one alkyne and at least one alkadiene from a stream, the process comprising:
a) contacting said stream with a metal-containing catalyst in the presence of a total molar ratio of at least about 0.5:1, of at least one of at least one alkyne and at least one alkadiene to said at least one ether and optionally in the presence of hydrogen, under conditions sufficient to convert the said at least one ether to at least one other oxygenate, thereby reducing the content of said at least one ether in said stream, and
b) exposing said stream with a metal-containing catalyst in the presence of hydrogen under conditions sufficient to at least partially convert said at least one of at least one alkyne and at least one alkadiene in said stream to at least one mono-olefin.

55. The process of claim 54 wherein said metal-containing catalyst in a) is different from said metal-containing catalyst in b).

56. The process of claim 54 wherein said metal-containing catalyst in a) is the same as said metal-containing catalyst in b).

57. The process of claim 54 wherein a) and b) are combined and carried out in-situ simultaneously.

58. The process of claim 54 wherein a) and b) are carried out in series and wherein a) is carried out prior to b).

59. The process of claim 54 wherein a) and b) are carried out in series and wherein b) is carried out prior to a).

60. The process of claim 54 wherein said at least one ether is $C_2$ to $C_6$ ether.

61. The process of claim 60 wherein said $C_2$ to $C_6$ ether is selected from dimethyl ether, methyl ethyl ether, methyl propyl ether, methyl butyl ether, diethyl ether, ethyl propyl ether, ethyl butyl ether, di-n-propyl ether, and di-isopropyl ether, said alkyne is selected from acetylene, methyl acetylene, ethyl acetylene and dimethyl acetylene, and said alkadiene is selected from propadiene, 1,2-butadiene and 1,3-butadiene.

62. The process of claim 60 wherein said at least one other oxygenate comprises at least one of $C_3$ to $C_{12}$ ether, $C_3$ to $C_{13}$ ketone and $C_3$ to $C_7$ aldehyde.

63. The process of claim 61 wherein said $C_2$ to $C_6$ ether comprises dimethyl ether, said alkyne comprises methyl acetylene, said alkadiene comprises propadiene and said treated stream comprises at least one of acetone, methyl n-propyl ether and methylisopropyl ether.

64. The process of claim 60 wherein said at least one other oxygenate comprises at least one oxygenate compound heavier than said $C_2$ to $C_6$ ether.

65. The process of claim 60 further comprises at least partially removing said at least one mono-olefin.

66. The process of claim 65 wherein said removing is carried out by distillation.

67. The process of claim 60 wherein said contacting conditions are vapor phase and comprise temperatures ranging from about 0° C. to about 800° C., total pressures ranging from about 101 kPaa to about 7 MPaa (from about 0 psig to about 1000 psig), GHSVs ranging from about 10 to about 30000, and hydrogen partial pressures ranging from about 0 kPaa to about 2170 kPaa (from about 0 psig to about 300 psig; and said exposing conditions comprise temperatures ranging from about 0° C. to about 800° C., total pressures ranging from about 101 kPaa to about 7 MPaa (from about 0 psig to about 1000 psig), GHSVs ranging from about 10 to about 30000, and hydrogen partial pressures ranging from about 0 kPaa to about 2170 kPaa (from about 0 psig to about 300 psig.

68. The process of claim 60 wherein said contacting conditions are vapor phase and comprise temperatures ranging from about 20° C. to about 600° C., total pressures ranging from about 101 kpaa to about 4240 kPaa (from about 0 psig to about 600 psig), GHSVs ranging from about 100 to about 20000, and hydrogen partial pressures ranging from about 0 kPaa to about 1480 kPaa (from about 0 psig to about 200 psig; and said exposing conditions comprise temperatures ranging from about 20° C. to about 600° C., total pressures ranging from about 101 kPaa to about 4240 kPaa (from about 0 psig to about 600 psig), GHSVs ranging from about 100 to about 20000 and hydrogen partial pressures ranging from about 0 kPaa to about 1480 kPaa (from about 0 psig to about 200 psig.

69. The process of claim 60 wherein said contacting conditions are liquid phase and comprise temperatures ranging from about 0° C. to about 100° C., total pressures ranging from about 790 kPaa to about 7 MPaa (from about 100 psig to about 1000 psig), LHSVs ranging from about 0.01 to about 1000, and a hydrogen/(alkyne+alkadiene) ratio ranging from about 0 to about 1000 on a molar basis; and said exposing conditions comprise temperatures ranging from about 0° C. to about 100° C., total pressures ranging from about 790 kPaa to about 7 MPaa (from about 100 psig to about 1000 psig), LHSVs ranging from about 0.01 to about 1000, and a hydrogen/(alkyne+alkadiene) ratio ranging from about 0 to about 1000 on a molar basis.

70. The process of claim 60 wherein said contacting conditions are liquid phase and comprise temperatures ranging from about 20° C. to about 80° C., total pressures ranging from about 1140 kPaa to about 4240 kPaa (from about 150 psig to about 600 psig), LHSVs ranging from about 0.1 to about 100, and a hydrogen/(alkyne+alkadiene) ratio ranging from about 0 to about 100 on a molar basis; and said exposing conditions comprise temperatures ranging from about 20° C. to about 80° C., total pressures ranging from about 1140 kPaa to about 4240 kPaa (from about 150 psig to about 600 psig), LHSVs ranging from about 0.1 to about 100, and a hydrogen/(alkyne+alkadiene) ratio ranging from about 0 to about 100 on a molar basis.

71. The process of claim 60 wherein said stream comprises from about 1 to about 5000 mppm dimethyl ether, from about 50 to about 100 wt % $C_2$ to $C_4$ olefin, and from about 1 mppm to about 20 mol % of said at least one of at least one alkyne and at least one alkadiene.

72. The process of claim 71 wherein said contacting and said exposing are carried out without substantially converting said $C_2$ to $C_4$ olefin.

73. The process of claim 60 wherein said stream comprises from about 1 to about 1000 mppm dimethyl ether, from about 75 to about 100 wt % $C_2$ to $C_4$ olefin, and from about 1 mppm to about 10 mol % of said at least one of an alkyne and an alkadiene.

74. The process of claim 60 wherein said stream comprises from about 1 to about 500 mppm dimethyl ether, from about 75 to 100 wt % propylene, from about 1 mppm to about 4 mol % methyl acetylene, and from about 1 mppm to about 5 mol % propadiene.

75. The process of claim 60 wherein at least about 20 mol % of said $C_2$ to $C_6$ ether and at least about 20 mol % of said at least one of at least one alkyne and at least one alkadiene are converted.

76. The process of claim 63 wherein at least about 50 mol % of said dimethyl ether and at least about 50 mol % of the total of said at least one of methyl acetylene and propadiene are converted.

77. The process of claim 60 wherein said exposing provides at least partial hydrogenation of said at least one of at least one alkyne and at least one alkadiene, of at least about 20 mol %.

78. The process of claim 77 wherein said at least partial hydrogenation provides at least one of ethylene, propylene, 1-butene, 2-butene and isobutene.

79. The process of claim 60 wherein said metal-containing catalyst in a) comprises i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one of at least one porous inorganic oxide, at least one microporous crystalline molecular sieve, and a carbon.

80. The process of claim 60 wherein said catalyst in a) comprises palladium.

81. The process of claim 60 wherein said catalyst in a) comprises palladium and silver.

82. The process of claim 60 wherein said catalyst in a) comprises at least one of i) at least one porous inorganic oxide selected from oxides of elements selected from group 2, group 3, group 4, group 5, Zn, group 13, Si, Ge, Sn, Pb, P, As, Sb and Bi, ii) at least one microporous crystalline molecular sieve selected from silicates, aluminosilicates, substituted aluminosilicates, aluminophosphates, and substituted aluminophosphates, and a carbon.

83. The process of claim 82 wherein said catalyst in a) further comprises iv) at least one of a sulfur-containing moiety and oxygen-containing moiety.

84. The process of claim 79 wherein said catalyst in a) comprises palladium on an alumina substrate and contains from about 0.01 to about 4.0 wt % palladium.

85. The process of claim 60 wherein said metal-containing catalyst in b) comprises i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one of at least one porous inorganic oxide, at least one microporous crystalline molecular sieve, and a carbon.

86. The process of claim 60 wherein said catalyst in b) comprises palladium.

87. The process of claim 60 wherein said catalyst in b) comprises palladium and silver.

88. The process of claim 60 wherein said catalyst in b) comprises at least one of i) at least one porous inorganic oxide selected from oxides of elements selected from group 2, group 3, group 4, group 5, Zn, group 13, Si, Ge, Sn, Pb, P, As, Sb and Bi, ii) at least one microporous crystalline molecular sieve selected from silicates, aluminosilicates, substituted aluminosilicates, aluminophosphates, and substituted aluminophosphates, and a carbon.

89. The process of claim 82 wherein said catalyst in b) further comprises iv) at least one of a sulfur-containing moiety and oxygen-containing moiety.

90. The process of claim 79 wherein said catalyst in b) comprises palladium on an alumina substrate and contains from about 0.01 to about 4.0 wt % palladium.

91. The process of claim 60 wherein a) and b) are carried out under substantially the same conditions.

92. The process of claim 60 wherein a) and b) are carried out under substantially different conditions.

93. A process for removing dimethyl ether from an olefin stream containing propylene, the process comprising:
contacting said olefin stream in the presence of a metal-containing catalyst and at least one of methyl acetylene and propadiene under conditions sufficient to convert at least some of said dimethyl ether to another oxygenate.

94. The process of claim 93 wherein said another oxygenate is heavier than the dimethyl ether; and which further comprises at least partially removing said another oxygenate.

95. The process of claim 94 wherein said removing is carried out by distillation.

96. The process of claim 93 wherein said conditions are vapor phase and comprise temperatures ranging from about 0° C. to about 800° C., total pressures ranging from about 101 kPaa to about 7 MPaa (from about 0 psig to about 1000 psig), GHSVs ranging from about 10 to about 30000, and hydrogen partial pressures ranging from about 0 kPaa to about 2170 kPaa (from about 0 psig to about 300 psig).

97. The process of claim 93 wherein said conditions are vapor phase and comprise temperatures ranging from about 20° C. to about 600° C., total pressures ranging from about 101 kPaa to about 4240 kPaa (from about 0 psig to about 600 psig), GHSVs ranging from about 100 to about 20000, and hydrogen partial pressures ranging from about 0 kPaa to about 1480 kpaa (from about 0 psig to about 200 psig).

98. The process of claim 93 wherein said conditions are liquid phase and comprise temperatures ranging from about 0° C. to about 100° C., total pressures ranging from about 790 kpaa to about 7 MPaa (from about 100 psig to about 1000 psig), LHSVs ranging from about 0.01 to about 1000, and a hydrogen/(alkyne+alkadiene) ratio ranging from about 0 to about 1000 on a molar basis.

99. The process of claim 93 wherein said conditions are liquid phase and comprise temperatures ranging from about 20° C. to about 80° C., total pressures ranging from about 1140 kPaa to about 4240 kPaa (from about 150 psig to about 600 psig), LHSVs ranging from about 0.1 to about 100, and a hydrogen/(alkyne+alkadiene) ratio ranging from about 0 to about 100 on a molar basis.

100. The process of claim 93 wherein said olefin stream comprises from about 1 to about 5000 mppm dimethyl ether, from about 50 to about 100 wt % propylene, and from about 1 mppm to about 20 mol % of said at least one of methyl acetylene and propadiene.

101. The process of claim 100 wherein said contacting is carried out without substantially converting said propylene.

102. The process of claim 93 wherein said olefin stream comprises from about 1 to about 1000 mppm dimethyl ether, from about 75 to about 100 wt % propylene, and from about 1 mppm to about 10 mol % of said at least one of methyl acetylene and propadiene.

103. The process of claim 93 wherein said olefin stream comprises from about 1 ppm to about 500 mppm dimethyl ether, from about 75 to about 100 wt % propylene, from about 1 mppm to about 4 mol % methyl acetylene, and from about 1 mppm to about 5 mol % propadiene.

104. The process of claim 93 wherein at least about 20 mol % of said dimethyl ether and at least about 20 mol % of said at least one of methyl acetylene and propadiene are converted.

105. The process of claim 93 wherein said metal-containing catalyst comprises i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one of at least one porous inorganic oxide, at least one microporous crystalline molecular sieve, and a carbon.

106. The process of claim 105 wherein said catalyst comprises palladium.

107. The process of claim 105 wherein said catalyst comprises palladium and silver.

108. The process of claim 93 wherein said catalyst comprises at least one of i) at least one porous inorganic oxide selected from oxides of elements selected from group 2, group 3, group 4, group 5, Zn, group 13, Si, Ge, Sn, Pb, P, As, Sb and Bi, ii) at least one microporous crystalline molecular sieve selected from silicates, aluminosilicates, substituted aluminosilicates, aluminophosphates, and substituted aluminophosphates, and a carbon.

109. The process of claim 108 wherein said catalyst further comprises iv) at least one of a sulfur-containing moiety and oxygen-containing moiety.

110. The process of claim 106 wherein said catalyst comprises palladium on an alumina substrate and contains from about 0.01 to about 4.0 wt % palladium.

* * * * *